US011911165B2

(12) United States Patent
Nathan et al.

(10) Patent No.: US 11,911,165 B2
(45) Date of Patent: Feb. 27, 2024

(54) SYSTEMS AND METHODS FOR ATRIAL FIBRILLATION BURDEN ESTIMATION, NOTIFICATION AND MANAGEMENT IN DAILY FREE-LIVING SCENARIOS

(71) Applicant: Samsung Electronics Co., Ltd., Suwon-si (KR)

(72) Inventors: Viswam Nathan, Sunnyvale, CA (US); Li Zhu, Milpitas, CA (US); Md Mahbubur Rahman, San Jose, CA (US); Jilong Kuang, San Jose, CA (US); Jun Gao, Menlo Park, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 355 days.

(21) Appl. No.: 17/115,561

(22) Filed: Dec. 8, 2020

(65) Prior Publication Data

US 2022/0175300 A1 Jun. 9, 2022

(51) Int. Cl.
| | |
|---|---|
| *A61B 5/361* | (2021.01) |
| *G16H 50/30* | (2018.01) |
| *G16H 50/70* | (2018.01) |
| *G16H 10/60* | (2018.01) |
| *A61B 5/00* | (2006.01) |
| *A61B 5/11* | (2006.01) |
| *G16H 40/67* | (2018.01) |
| *G16H 50/50* | (2018.01) |
| *A61B 5/339* | (2021.01) |
| *G16H 20/30* | (2018.01) |

(52) U.S. Cl.
CPC ............ *A61B 5/361* (2021.01); *A61B 5/1118* (2013.01); *A61B 5/339* (2021.01); *A61B 5/486* (2013.01); *A61B 5/6898* (2013.01); *G16H 10/60* (2018.01); *G16H 20/30* (2018.01); *G16H 40/67* (2018.01); *G16H 50/30* (2018.01); *G16H 50/50* (2018.01); *G16H 50/70* (2018.01)

(58) Field of Classification Search
CPC ....... A61B 5/361; A61B 5/339; A61B 5/1118; A61B 5/486; A61B 5/6898; G16H 20/30; G16H 40/67; G16H 50/50; G16H 10/60; G16H 50/30; G16H 50/70
See application file for complete search history.

(56) References Cited

U.S. PATENT DOCUMENTS

| | | | |
|---|---|---|---|
| 8,874,200 | B2 | 10/2014 | Bardy |
| 9,913,587 | B2 | 3/2018 | Poh |
| 10,098,559 | B2 | 10/2018 | Hughes et al. |

(Continued)

FOREIGN PATENT DOCUMENTS

| | | | | |
|---|---|---|---|---|
| KR | 20160147516 A | 12/2016 | | |
| WO | WO-2020086865 A1 | * | 4/2020 | ............ A61B 5/333 |

*Primary Examiner* — Carl H Layno
*Assistant Examiner* — Aya Ziad Bakkar

(57) ABSTRACT

A method includes estimating, by a consumer electronic device, an atrial fibrillation (AF) burden of a subject based on multiple measurements passively collected by at least one sensor associated with the consumer electronic device while the subject is in a free-living environment. The method also includes outputting, by the consumer electronic device, an AF burden notification associated with the subject based on the estimated AF burden. The method further includes outputting, by the consumer electronic device, an AF burden recommendation based on the estimated AF burden.

20 Claims, 13 Drawing Sheets

(56) References Cited

U.S. PATENT DOCUMENTS

| | | |
|---|---|---|
| 10,561,321 B2 | 2/2020 | Valys et al. |
| 10,758,139 B2 | 9/2020 | Rapin et al. |
| 2002/0029002 A1* | 3/2002 | Bardy .................. A61B 5/361 |
| | | 600/518 |
| 2018/0247713 A1* | 8/2018 | Rothman ........... A61B 5/02055 |
| 2019/0133468 A1 | 5/2019 | Aliamiri et al. |
| 2020/0229713 A1 | 7/2020 | Gopalakrishnan et al. |
| 2020/0245886 A1 | 8/2020 | Qu et al. |

* cited by examiner

Prior Probability ⟶ 501

| State | Probability |
|---|---|
| α | $\pi_\alpha \in (0,1)$ The probability that the Markov chain begins with state α |
| β | $\pi_\beta \in (0,1)$ The probability that the Markov chain begins with state β |

FIG. 5A

Transition Probability ⟶ 502

| State | α | β |
|---|---|---|
| α | $s_{\alpha\alpha} \in (0,1)$ The probability of moving from state α to state α | $s_{\alpha\beta} \in (0,1)$ The probability of moving from state α to state β |
| β | $s_{\beta\alpha} \in (0,1)$ The probability of moving from state β to state α | $s_{\beta\beta} \in (0,1)$ The probability of moving from state β to state β |

FIG. 5B

| Obsrv | Emission Probability | |
|---|---|---|
| | α | β |
| $o_p$ | $b_\alpha(o_p) \in (0,1)$ The probability of an observation $o_p$ being generated from state α | $b_\beta(o_p) \in (0,1)$ The probability of an observation $o_p$ being generated from state β |
| $o_q$ | $b_\alpha(o_q) \in (0,1)$ The probability of an observation $o_q$ being generated from state α | $b_\beta(o_q) \in (0,1)$ The probability of an observation $o_q$ being generated from state β |
| $o_r$ | $b_\alpha(o_r) \in (0,1)$ The probability of an observation $o_r$ being generated from state α | $b_\beta(o_r) \in (0,1)$ The probability of an observation $o_r$ being generated from state β |
| $o_s$ | $b_\alpha(o_s) \in (0,1)$ The probability of an observation $o_s$ being generated from state α | $b_\beta(o_s) \in (0,1)$ The probability of an observation $o_s$ being generated from state β |

Prior Probability ⟵ 501

| State | Probability |
|---|---|
| NSR | 0.8 |
| AF | 0.2 |

FIG. 6A

Transition Probability ⟵ 502

| State | NSR | AF |
|---|---|---|
| NSR | 0.9 | 0.1 |
| AF | 0.3 | 0.7 |

FIG. 6B

Emission Probability ⟵ 503

| Observation | NSR | AF |
|---|---|---|
| AF Decision, Resting | 0.3 | 0.7 |
| NSR Decision, Resting | 0.9 | 0.1 |
| AF Decision, Running | 0.6 | 0.4 |
| NSR Decision, Running | 0.8 | 0.2 |

FIG. 6C

SYSTEMS AND METHODS FOR ATRIAL FIBRILLATION BURDEN ESTIMATION, NOTIFICATION AND MANAGEMENT IN DAILY FREE-LIVING SCENARIOS

TECHNICAL FIELD

This disclosure relates generally to health monitoring systems and methods. More specifically, this disclosure relates to systems and methods for atrial fibrillation burden estimation, notification and management in daily free-living scenarios.

BACKGROUND

Recent technological advances in sensing capabilities, wearable devices, and artificial intelligence (AI) are transforming health care by shifting from classical hospitals or clinics to patient centered health care. The transformation enables proactive mobile health and facilitates low-cost unobtrusive solutions for health activity monitoring. Passive and mobile health monitoring can be applied to different applications of general health, fitness tracking, and adverse health event prediction.

Some recent technologies allow passive and continuous monitoring of heart rhythms, specifically to detect atrial fibrillation (AF). One advantage of continuous and longitudinal monitoring is the ability to estimate AF burden, an increasingly important parameter in characterizing the severity of the illness. AF burden is a measure of the amount of time per day that the individual is under an AF condition, and a higher burden means increased likelihood of adverse consequences. However, it can be difficult to accurately estimate and analyze AF burden in free-living scenarios, where the subject is not in a controlled environment.

SUMMARY

This disclosure provides systems and methods for atrial fibrillation burden estimation, notification and management in daily free-living scenarios.

In a first embodiment, a method includes estimating, by a consumer electronic device, an atrial fibrillation (AF) burden of a subject based on multiple measurements passively collected by at least one sensor associated with the consumer electronic device while the subject is in a free-living environment. The method also includes outputting, by the consumer electronic device, an AF burden notification associated with the subject based on the estimated AF burden. The method further includes outputting, by the consumer electronic device, an AF burden recommendation based on the estimated AF burden.

In a second embodiment, an electronic device includes at least one memory configured to store instructions. The electronic device also includes a processor configured when executing the instructions to estimate an AF burden of a subject based on multiple measurements passively collected by at least one sensor associated with the electronic device while the subject is in a free-living environment. The processor is also configured to output an AF burden notification associated with the subject based on the estimated AF burden. The processor is further configured to output an AF burden recommendation based on the estimated AF burden. The electronic device is a consumer electronic device.

In a third embodiment, a non-transitory computer readable medium contains computer readable program code that, when executed, causes at least one processor of an electronic device to estimate an AF burden of a subject based on multiple measurements passively collected by at least one sensor associated with the electronic device while the subject is in a free-living environment; output an AF burden notification associated with the subject based on the estimated AF burden; and output an AF burden recommendation based on the estimated AF burden, wherein the electronic device is a consumer electronic device.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

As used here, terms and phrases such as "have," "may have," "include," or "may include" a feature (like a number, function, operation, or component such as a part) indicate the existence of the feature and do not exclude the existence of other features. Also, as used here, the phrases "A or B," "at least one of A and/or B," or "one or more of A and/or B" may include all possible combinations of A and B. For example, "A or B," "at least one of A and B," and "at least one of A or B" may indicate all of (1) including at least one A, (2) including at least one B, or (3) including at least one A and at least one B.

As used here, the terms "first" and "second" may modify various components regardless of importance and do not limit the components. These terms are only used to distinguish one component from another. For example, a first user device and a second user device may indicate different user devices from each other, regardless of the order or importance of the devices. A first component may be denoted a second component and vice versa without departing from the scope of this disclosure.

It will be understood that, when an element (such as a first element) is referred to as being (operatively or communicatively) "coupled with/to" or "connected with/to" another element (such as a second element), it can be coupled or connected with/to the other element directly or via a third element. In contrast, it will be understood that, when an element (such as a first element) is referred to as being "directly coupled with/to" or "directly connected with/to" another element (such as a second element), no other element (such as a third element) intervenes between the element and the other element.

As used here, the phrase "configured (or set) to" may be interchangeably used with the phrases "suitable for," "having the capacity to," "designed to," "adapted to," "made to," or "capable of" depending on the circumstances. The phrase "configured (or set) to" does not essentially mean "specifically designed in hardware to." Rather, the phrase "configured to" may mean that a device can perform an operation together with another device or parts. For example, the phrase "processor configured (or set) to perform A, B, and C" may mean a generic-purpose processor (such as a CPU or application processor) that may perform the operations by executing one or more software programs stored in a memory device or a dedicated processor (such as an embedded processor) for performing the operations.

The terms and phrases as used here are provided merely to describe some embodiments of this disclosure but not to limit the scope of other embodiments of this disclosure. It is to be understood that the singular forms "a," "an," and "the" include plural references unless the context clearly dictates otherwise. All terms and phrases, including technical and scientific terms and phrases, used here have the same meanings as commonly understood by one of ordinary skill in the art to which the embodiments of this disclosure belong. It will be further understood that terms and phrases, such as those defined in commonly-used dictionaries, should be interpreted as having a meaning that is consistent with their meaning in the context of the relevant art and will not be interpreted in an idealized or overly formal sense unless expressly so defined here. In some cases, the terms and phrases defined here may be interpreted to exclude embodiments of this disclosure.

Examples of an "electronic device" according to embodiments of this disclosure may include at least one of a smart phone, a tablet personal computer (PC), a mobile phone, a video phone, an e-book reader, a desktop PC, a laptop computer, a netbook computer, a workstation, a personal digital assistant (PDA), a portable multimedia player (PMP), an MP3 player, a mobile medical device, a camera, or a wearable device (such as smart glasses, a head-mounted device (HMD), electronic clothes, an electronic bracelet, an electronic necklace, an electronic appcessory, an electronic tattoo, a smart mirror, or a smart watch). Other examples of an electronic device include a smart home appliance. Examples of the smart home appliance may include at least one of a television, a digital video disc (DVD) player, an audio player, a refrigerator, an air conditioner, a cleaner, an oven, a microwave oven, a washer, a drier, an air cleaner, a set-top box, a home automation control panel, a security control panel, a TV box (such SAMSUNG HOMESYNC, APPLETV, or GOOGLE TV), a gaming console (such as an XBOX, PLAYSTATION, or NINTENDO), an electronic dictionary, an electronic key, a camcorder, or an electronic picture frame. Still other examples of an electronic device include at least one of various medical devices (such as diverse portable medical measuring devices (like a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global positioning system (GPS) receiver, an event data recorder (EDR), a flight data recorder (FDR), an automotive infotainment device, a sailing electronic device (such as a sailing navigation device or a gyro compass), avionics, security devices, vehicular head units, industrial or home robots, automatic teller machines (ATMs), point of sales (POS) devices, or Internet of Things (IoT) devices (such as a bulb, various sensors, electric or gas meter, sprinkler, fire alarm, thermostat, street light, toaster, fitness equipment, hot water tank, heater, or boiler). Other examples of an electronic device include at least one part of a piece of furniture or building/structure, an electronic board, an electronic signature receiving device, a projector, or various measurement devices (such as devices for measuring water, electricity, gas, or electromagnetic waves). Note that, according to embodiments of this disclosure, an electronic device may be one or a combination of the above-listed devices. According to some embodiments of this disclosure, the electronic device may be a flexible electronic device. The electronic device disclosed here is not limited to the above-listed devices and may include new electronic devices depending on the development of technology.

In the following description, electronic devices are described with reference to the accompanying drawings, according to embodiments of this disclosure. As used here, the term "user" may denote a human or another device (such as an artificial intelligent electronic device) using the electronic device.

Definitions for other certain words and phrases may be provided throughout this patent document. Those of ordinary skill in the art should understand that in many if not most instances, such definitions apply to prior as well as future uses of such defined words and phrases.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle. Use of any other term, including without limitation "mechanism," "module," "device," "unit," "component," "element," "member," "apparatus," "machine," "system," "processor," or "controller," within a claim is understood by the Applicant to refer to structures known to those skilled in the relevant art and is not intended to invoke 35 U.S.C. § 112(f).

BRIEF DESCRIPTION OF THE DRAWINGS

For a more complete understanding of this disclosure and its advantages, reference is now made to the following description, taken in conjunction with the accompanying drawings, in which:

FIGS. 5A through 5C illustrate probability matrices that can be used in the HMM architecture of FIG. 4 in accordance with this disclosure;

FIGS. 6A through 6C illustrate examples of probability matrices populated with initial values for use in AF burden estimation, in accordance with this disclosure;

DETAILED DESCRIPTION

The figures discussed below and the various embodiments used to describe the principles of this disclosure in this patent document are by way of illustration only and should not be construed in any way to limit the scope of the disclosure. Those skilled in the art will understand that the principles of this disclosure can be implemented in any suitably arranged system.

Recent data indicates that up to 6.1 million people in the United States, including 9% of all people aged over 65, suffer from atrial fibrillation (AF). This number is expected to rise to 12.1 million in 2030. AF increases the risk of stroke by 5×, the risk of heart failure by 5×, and the risk of cardiovascular mortality by 2×. Some recently developed technologies allow passive and continuous monitoring of heart rhythms, specifically to detect AF. One advantage of continuous and longitudinal monitoring is the ability to estimate AF burden. As discussed above, a higher AF burden means an increased likelihood of adverse consequences, such as stroke and greater cognitive risk. However, it can be difficult to accurately estimate and analyze AF burden in free-living scenarios, where the subject is not in a controlled environment.

For example, spot-checks during sporadic clinic visits are insufficient to characterize burden. Conversely, accurate ECG-based systems are not feasible to be worn continuously, have limited battery life, and are not designed to be recharged and re-used for extended periods like wearables, and are also inconvenient for the subject. Convenient wearable rhythm detecting solutions have not shown sufficient accuracy in free-living scenarios, and also only aim to detect the presence or absence of AF, not the AF burden. In addition, existing solutions do not notify the subject about their AF burden, nor do they provide methods to reduce the AF burden.

To address these and other issues, embodiments of this disclosure provide systems and methods for AF burden estimation, notification and management in daily free-living scenarios. The disclosed systems and methods are capable of using mobile sensors, such as those found on smart phones and smart watches, to passively estimate daily AF burden, appropriately notify the subject on the findings, and provide a personalized recommendation to the subject for a way to reduce the burden and hence reduce health risks.

Figure 1:
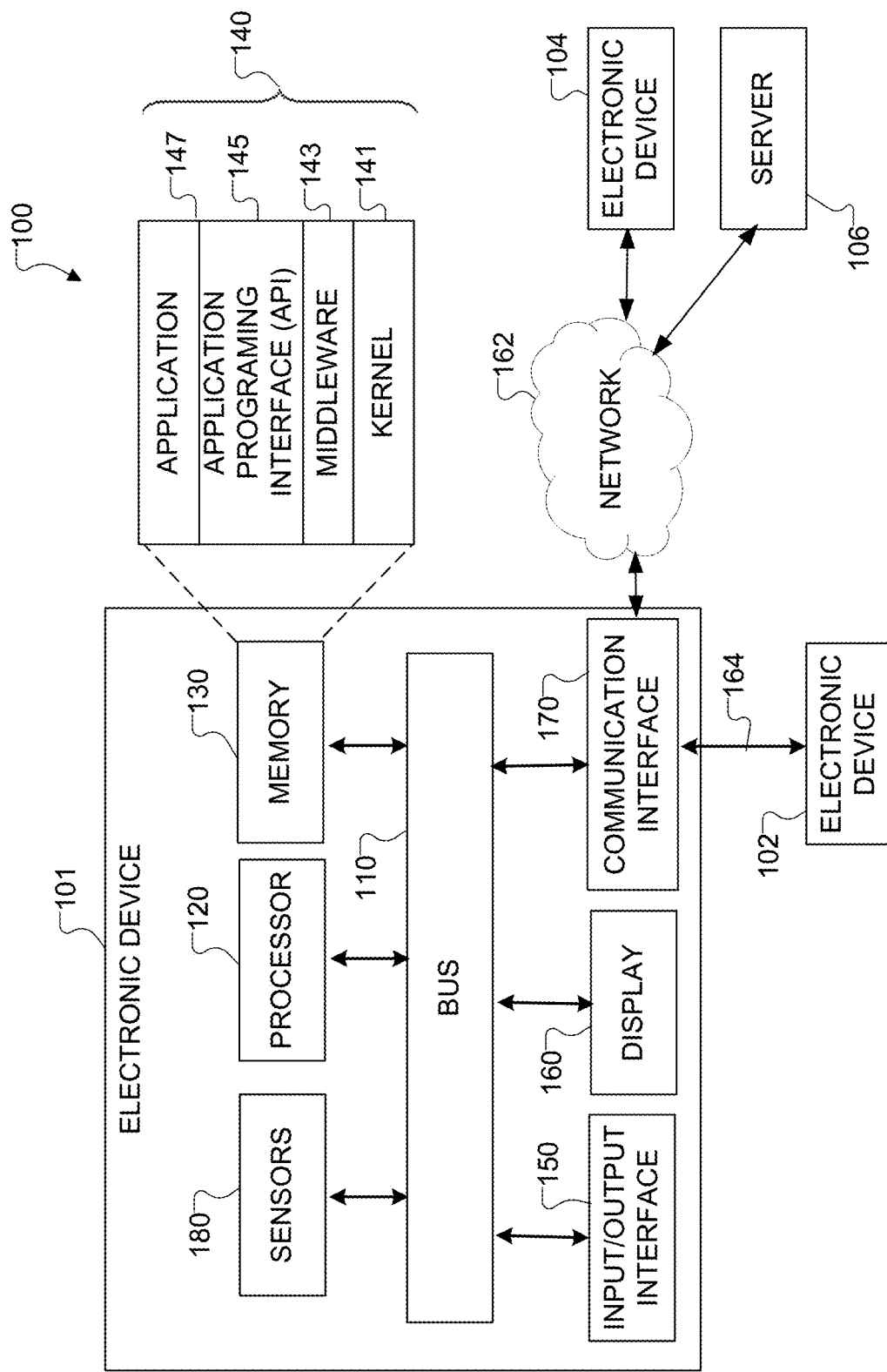
FIG. 1 illustrates an example network configuration in accordance with this disclosure.

FIG. 1 illustrates an example network configuration 100 in accordance with this disclosure. As shown in FIG. 1, according to embodiments of this disclosure, an electronic device 101 is included in the network configuration 100. The electronic device 101 may include at least one of a bus 110, a processor 120, a memory 130, an input/output (I/O) interface 150, a display 160, a communication interface 170, or a sensor 180. In some embodiments, the electronic device 101 may exclude at least one of the components or may add another component.

The bus 110 may include a circuit for connecting the components 120-180 with one another and transferring communications (such as control messages and/or data) between the components. The processor 120 may include one or more of a central processing unit (CPU), an application processor (AP), or a communication processor (CP). The processor 120 may perform control on at least one of the other components of the electronic device 101 and/or perform an operation or data processing relating to communication.

The memory 130 may include a volatile and/or non-volatile memory. For example, the memory 130 may store commands or data related to at least one other component of the electronic device 101. According to embodiments of this disclosure, the memory 130 may store software and/or a program 140. The program 140 may include, for example, a kernel 141, middleware 143, an application programming interface (API) 145, and/or an application program (or "application") 147. At least a portion of the kernel 141, middleware 143, or API 145 may be denoted an operating system (OS).

The kernel 141 may control or manage system resources (such as the bus 110, processor 120, or memory 130) used to perform operations or functions implemented in other programs (such as the middleware 143, API 145, or application program 147). The kernel 141 may provide an interface that allows the middleware 143, API 145, or application 147 to access the individual components of the electronic device 101 to control or manage the system resources. The middleware 143 may function as a relay to allow the API 145 or the application 147 to communicate data with the kernel 141, for example. A plurality of applications 147 may be provided. The middleware 143 may control work requests received from the applications 147, such as by allocating the priority of using the system resources of the electronic device 101 (such as the bus 110, processor 120, or memory 130) to at least one of the plurality of applications 147. The API 145 is an interface allowing the application 147 to control functions provided from the kernel 141 or the middleware 143. For example, the API 145 may include at least one interface or function (such as a command) for file control, window control, image processing, or text control.

The input/output interface 150 may serve as an interface that may, for example, transfer commands or data input from a user or other external devices to other component(s) of the electronic device 101. Further, the input/output interface 150 may output commands or data received from other component(s) of the electronic device 101 to the user or the other external devices.

The display 160 may include, for example, a liquid crystal display (LCD), a light emitting diode (LED) display, an organic light emitting diode (OLED) display, an active matrix OLED (AMOLED), a microelectromechanical systems (MEMS) display, or an electronic paper display. The display 160 can also be a depth-aware display, such as a multi-focal display. The display 160 may display various contents (such as text, images, videos, icons, or symbols) to the user. The display 160 may include a touchscreen and may receive, for example, a touch, gesture, proximity, or hovering input using an electronic pen or a body portion of the user.

The communication interface 170 may set up communication between the electronic device 101 and an external electronic device (such as a first electronic device 102, a second electronic device 104, or a server 106). For example, the communication interface 170 may be connected with a network 162 or 164 through wireless or wired communication to communicate with the external electronic device.

The electronic device 101 further includes one or more sensors 180 that can meter a physical quantity or detect an activation state of the electronic device 101 and convert metered or detected information into an electrical signal. For example, one or more sensors 180 can include one or more buttons for touch input, one or more cameras, a gesture sensor, a gyroscope or gyro sensor, an air pressure sensor, a magnetic sensor or magnetometer, an acceleration sensor or accelerometer, a grip sensor, a proximity sensor, a color sensor (such as a red green blue (RGB) sensor), a bio-physical sensor, a temperature sensor, a humidity sensor, an illumination sensor, an ultraviolet (UV) sensor, an electro-myography (EMG) sensor, an electroencephalogram (EEG) sensor, an electrocardiogram (ECG) sensor, an infrared (IR) sensor, an ultrasound sensor, an iris sensor, or a fingerprint sensor. The sensor(s) 180 can also include an inertial measurement unit, which can include one or more accelerometers, gyroscopes, and other components. The sensor(s) 180 can further include a control circuit for controlling at least one of the sensors included here. Any of these sensor(s) 180 can be located within the electronic device 101.

The first external electronic device 102 or the second external electronic device 104 may be a wearable device or an electronic device 101-mountable wearable device (such as a head mounted display (HMD)). When the electronic device 101 is mounted in an HMD (such as the electronic device 102), the electronic device 101 may detect the mounting in the HMD and operate in a virtual reality mode. When the electronic device 101 is mounted in the electronic device 102 (such as the HMD), the electronic device 101 may communicate with the electronic device 102 through the communication interface 170. The electronic device 101 may be directly connected with the electronic device 102 to communicate with the electronic device 102 without involving with a separate network.

The wireless communication may use at least one of, for example, long term evolution (LTE), long term evolution-advanced (LTE-A), code division multiple access (CDMA), wideband code division multiple access (WCDMA), universal mobile telecommunication system (UMTS), wireless broadband (WiBro), or global system for mobile communication (GSM), as a cellular communication protocol. The wired connection may include at least one of, for example, universal serial bus (USB), high definition multimedia interface (HDMI), recommended standard 232 (RS-232), or plain old telephone service (POTS). The network 162 may include at least one communication network, such as a computer network (like a local area network (LAN) or wide area network (WAN)), the Internet, or a telephone network.

The first and second external electronic devices 102 and 104 each may be a device of the same type or a different type from the electronic device 101. According to embodiments of this disclosure, the server 106 may include a group of one or more servers. Also, according to embodiments of this disclosure, all or some of the operations executed on the electronic device 101 may be executed on another or multiple other electronic devices (such as the electronic devices 102 and 104 or server 106). Further, according to embodiments of this disclosure, when the electronic device 101 should perform some function or service automatically or at a request, the electronic device 101, instead of executing the function or service on its own or additionally, may request another device (such as electronic devices 102 and 104 or server 106) to perform at least some functions associated therewith. The other electronic device (such as electronic devices 102 and 104 or server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technique may be used, for example.

While FIG. 1 shows that the electronic device 101 includes the communication interface 170 to communicate with the external electronic device 102 or 104 or server 106 via the network(s) 162 and 164, the electronic device 101 may be independently operated without a separate communication function, according to embodiments of this disclosure. Also, note that the electronic device 102 or 104 or the server 106 could be implemented using a bus, a processor, a memory, an I/O interface, a display, a communication interface, and an event processing module (or any suitable subset thereof) in the same or similar manner as shown for the electronic device 101.

Although FIG. 1 illustrates one example of a network configuration 100, various changes may be made to FIG. 1. For example, the network configuration 100 could include any number of each component in any suitable arrangement. In general, computing and communication systems come in a wide variety of configurations, and FIG. 1 does not limit the scope of this disclosure to any particular configuration. Also, while FIG. 1 illustrates one operational environment in which various features disclosed in this patent document can be used, these features could be used in any other suitable system.

Figure 2:
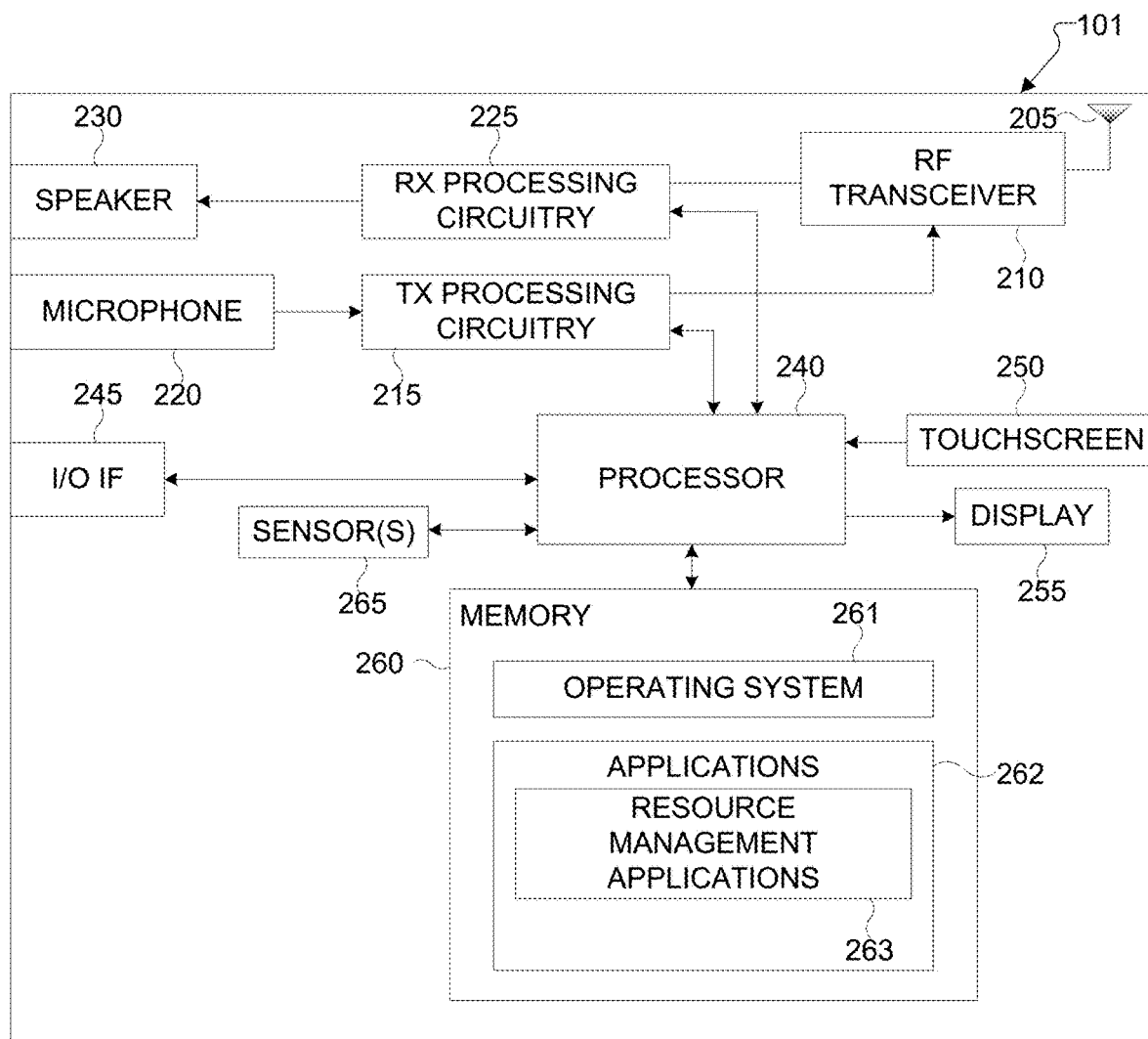
FIG. 2 illustrates an example electronic device in accordance with this disclosure.

FIG. 2 illustrates an example electronic device 101 in accordance with this disclosure. The electronic device 101 could represent one or more of the electronic devices 101, 102, or 104 in FIG. 1. As shown in FIG. 2, the electronic device 101 includes an antenna 205, a radio frequency (RF) transceiver 210, transmit (TX) processing circuitry 215, a microphone 220, and receive (RX) processing circuitry 225. The electronic device 101 also includes a speaker 230, a processor 240, an input/output (I/O) interface (IF) 245, an input 250, a display 255, and a memory 260. The memory 260 includes an operating system (OS) program 261 and one or more applications 262.

The RF transceiver 210 receives, from the antenna 205, an incoming RF signal transmitted by another component in a system. The RF transceiver 210 down-converts the incoming RF signal to generate an intermediate frequency (IF) or baseband signal. The IF or baseband signal is sent to the RX processing circuitry 225, which generates a processed baseband signal by filtering, decoding, and/or digitizing the baseband or IF signal. The RX processing circuitry 225 transmits the processed baseband signal to the speaker 230 (such as for voice data) or to the processor 240 for further processing.

The TX processing circuitry 215 receives analog or digital voice data from the microphone 220 or other outgoing baseband data (such as web data, e-mail, or interactive video game data) from the processor 240. The TX processing circuitry 215 encodes, multiplexes, and/or digitizes the outgoing baseband data to generate a processed baseband or IF signal. The RF transceiver 210 receives the outgoing processed baseband or IF signal from the TX processing circuitry 215 and up-converts the baseband or IF signal to an RF signal that is transmitted via the antenna 205.

The processor 240 can include one or more processors or other processors and execute the OS program 261 stored in the memory 260 in order to control the overall operation of the electronic device 101. For example, the processor 240 could control the reception of forward channel signals and the transmission of reverse channel signals by the RF transceiver 210, the RX processing circuitry 225, and the TX processing circuitry 215 in accordance with well-known principles. In some embodiments, the processor 240 includes at least one microprocessor or microcontroller.

The processor 240 is also capable of executing other processes and programs resident in the memory 260. The processor 240 can move data into or out of the memory 260 as required by an executing process. In some embodiments, the processor 240 is configured to execute the applications 262 based on the OS program 261 or in response to signals received from external devices or an operator. The processor 240 can execute a resource management application 263 for monitoring system resources. The processor 240 is also coupled to the I/O interface 245, which provides the electronic device 101 with the ability to connect to other devices such as laptop computers, handheld computers and other accessories, for example, a virtual reality (VR) headset. The I/O interface 245 is the communication path between these accessories and the processor 240. The processor 240 can recognize accessories that are attached through the I/O interface 245, such as a VR headset connected to a USB port.

The processor 240 is also coupled to the input 250 and the display 255. The operator of the electronic device 101 can use the input 250 (e.g., keypad, touchscreen, button etc.) to enter data into the electronic device 101. The display 255 may be an LCD, LED, OLED, AMOLED, MEMS, electronic paper, or other display capable of rendering text and/or at least limited graphics, such as from web sites.

The memory 260 is coupled to the processor 240. Part of the memory 260 could include a random access memory (RAM), and another part of the memory 260 could include a Flash memory or other read-only memory (ROM).

The electronic device 101 further includes one or more sensors 265 that can meter a physical quantity or detect an activation state of the electronic device 101 and convert metered or detected information into an electrical signal. For example, the sensor 265 may include any of the various sensors 180 discussed above.

Although FIG. 2 illustrates one example of an electronic device 101, various changes may be made to FIG. 2. For example, various components in FIG. 2 could be combined, further subdivided, or omitted and additional components could be added according to particular needs. As a particular example, the processor 240 could be divided into multiple processors, such as one or more central processing units (CPUs) and one or more graphics processing units (GPUs). Also, while FIG. 2 illustrates the electronic device 101 configured as a mobile telephone or smart phone, electronic devices could be configured to operate as other types of mobile or stationary devices. In addition, as with computing and communication networks, electronic devices can come in a wide variety of configurations and FIG. 2 does not limit this disclosure to any particular electronic device.

Figure 3:
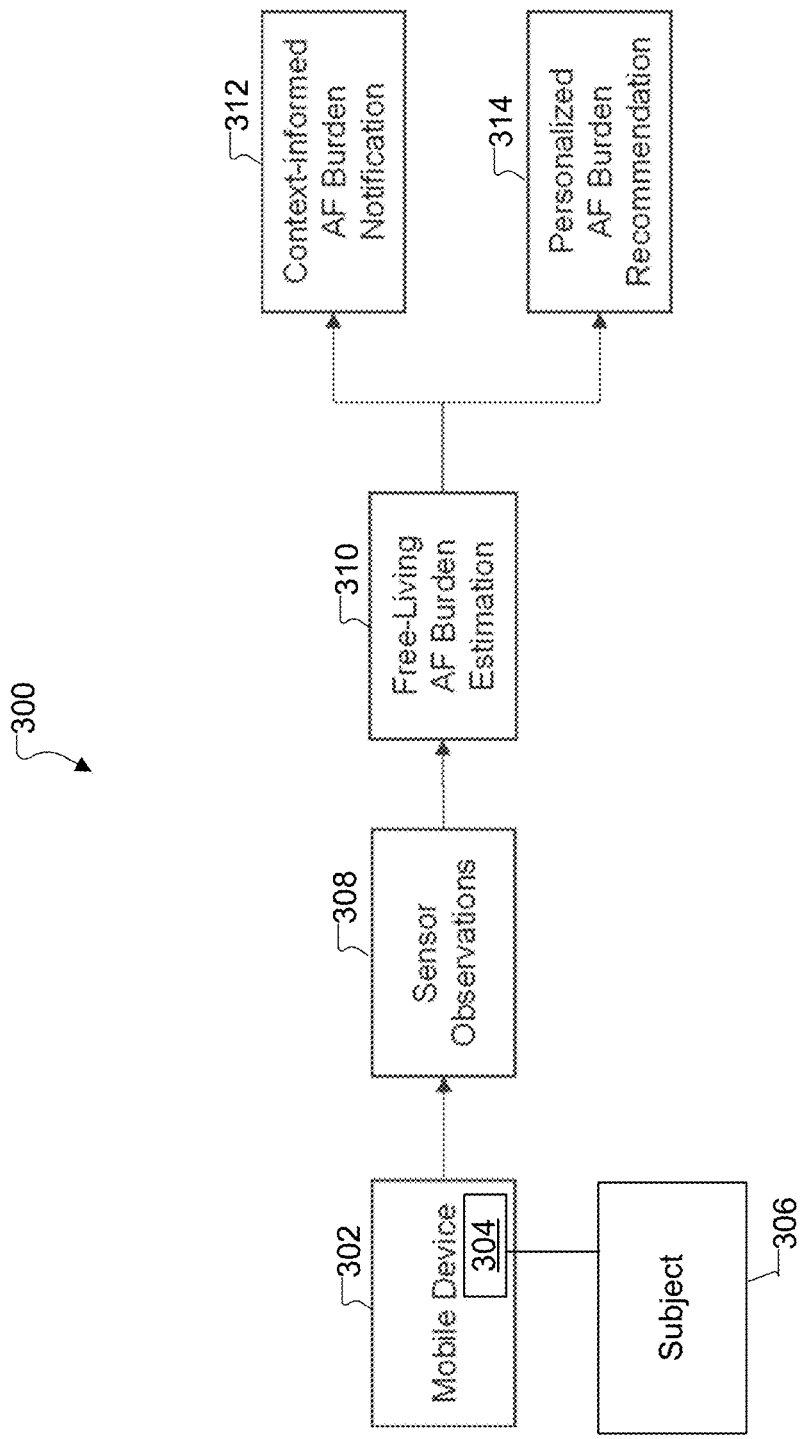
FIG. 3 illustrates an example process for atrial fibrillation (AF) burden estimation, notification, and management in accordance with this disclosure.

FIG. 3 illustrates an example process 300 for AF burden estimation, notification, and management in accordance with this disclosure. For ease of explanation, the process 300 is described as involving at least one electronic device (such as the electronic device 101 of FIG. 1). However, the process 300 could be used with any other suitable device or system without departing from the scope of this disclosure.

As shown in FIG. 3, the at least one electronic device comprises one or more mobile devices 302. For ease of explanation, the process 300 will be described further using one mobile device 302 as an example. However, it will be understood that multiple mobile devices 302 used together is permissible and within the scope of this disclosure. The mobile device 302 is a consumer electronic device, such as a smart phone, a smart watch, or the like. The mobile device 302 includes one or more sensors 304 that are capable of collecting or measuring data associated with a subject 306, who may be a user of the mobile device 302. The sensors 304 can represent (or be represented by) the sensors 180 of FIG. 1 or the sensors 265 of FIG. 2. For example, the sensors 304 can include one or more inertial measurement unit (IMU) sensors that measure the position, orientation, and movement of the subject 306; photoplethysmogram (PPG) sensors that measure blood pressure and oxygen saturation of the subject 306; GPS sensors that detect a location of the subject 306; clocks and calendars that track time and date; and the like. The data collected or measured by the sensors 304 can be aggregated and stored (e.g., in a memory 130) as sensor observations 308. At least some of the sensor observations 308 can be used for AF detection and AF burden estimation, as described below.

The sensors 304 passively collect data of the subject 306 and store the data as sensor observations 308 regularly or continuously over a long period of time (e.g., several days, weeks, or months) while the subject 306 lives in a free-living environment. As used herein, a free-living environment is an environment in which the subject would normally live and perform typical daily activities, such as at home, at work, or on-the-go. A free-living environment can be contrasted with a controlled environment in which the subject is subject to medical testing or health screening (e.g., a laboratory, medical facility, and the like) and/or the subject's activities are significantly restricted for medical testing or health screening.

Passive long-term monitoring using the sensors 304 provides a number of advantages over existing methods of assessing AF burden. While the collection of the data is referred to herein as regular or continuous, it will be understood that some temporal gaps can exist in the sensor observations 308, such as when a sensor 304 is turned off, not worn or carried by the subject 306, or is otherwise unable to collect accurate data. Gaps in the sensor observations 308 can also exist due to algorithm errors or noise and motion artifacts that naturally arise in free-living environments.

Once the mobile device 302 has obtained a quantity of sensor observations 308, the mobile device 302 performs an AF burden estimation operation 310 to estimate the AF burden of the subject 306. One function of the AF burden estimation operation 310 is to estimate the AF burden of the subject 306 in the presence of gaps in the sensor observations 308. In some embodiments, the mobile device 302 can use a Hidden Markov Model (HMM) to estimate AF burden when there are gaps in the sensor observations 308.

Figure 4:
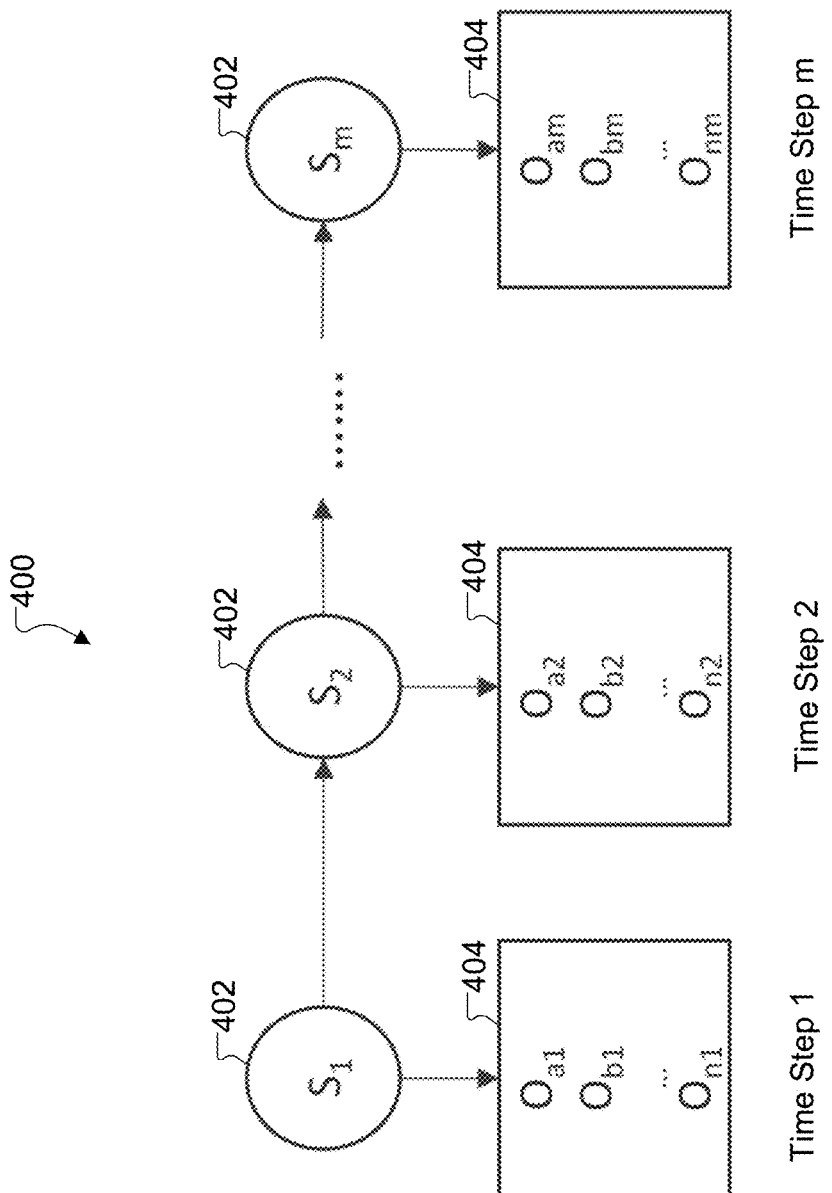
FIG. 4 illustrates an example Hidden Markov Model (HMM) architecture that can be used for AF burden estimation in accordance with this disclosure.

FIG. 4 illustrates an example HMM architecture 400 that can be used for AF burden estimation in accordance with this disclosure. As shown in FIG. 4, the HMI architecture 400 includes multiple states 402, where each state is associated with a time step. The states 402 are labeled as $S_1, S_2, \ldots, S_m$, where $S_t$ is the true state of the subject 306 at time step t. Step m represents the current time step. For the AF burden estimation operation 310, the states in the HMM architecture 400 can represent the true state of the heart rhythm of the subject 306. For example, the states $S_t$ can be either NSR (normal sinus rhythm, which is a normal condition of the subject 306) or AF (which indicates a state of AF or AF burden for the subject 306). Of course, additional or alternative states are possible and within the scope of this disclosure.

For each state 402, the HMM architecture 400 includes multiple observations 404, which are labeled $O_{a1}, O_{b1}, \ldots, O_{n1}, O_{a2}, O_{b2}, O_{n2}, O_{am}, O_{bm}, \ldots, O_{nm}$, where $O_{xt}$ is the observation 404 from sensor x at time step t, and n is the total number of sensor inputs available for the AF burden estimation operation 310. The observations 404 can be obtained from AF algorithm output, IMU sensor readings, and the like. In some embodiments, at least some of the observations 404 comprise sensor observations 308.

As known in the art, a HMM is modeled using multiple probability matrices. For example, FIGS. 5A through 5C illustrate probability matrices 501-503 that can be used in the HMI architecture 400 in accordance with this disclosure. In particular, FIG. 5A illustrates a prior probability matrix 501, FIG. 5B illustrates a transition probability matrix 502, and FIG. 5C illustrates an emission probability matrix 503. The prior probability matrix 501 includes multiple states, $\alpha$ and $\beta$, and probabilities that a Markov chain begins with each state. The transition probability matrix 502 includes the multiple states and probabilities of moving between the states or staying in an existing state. The emission probability matrix 503 includes a list of observations, such as the observations 404, and probabilities of an observation being generated from one of the states. While the matrices 501-503 are generally known in HMI modeling, the initialization, updating, and use of these matrices 501-503 in the AF burden estimation operation 310 is unique and advantageous, as described below.

FIGS. 6A through 6C illustrate examples of probability matrices 501-503 populated with initial values for use in AF burden estimation, in accordance with this disclosure. As shown in FIG. 6A, the prior probability matrix 501 is populated with two states, NSR and AF, and corresponding probabilities of the subject 306 being in either of these states at the start of the AF burden estimation operation 310. For example, there is an 80% probability (0.8 value) that the subject 306 will be in the NSR state at the start of the AF burden estimation operation 310, and only a 20% probability that the subject 306 will be in the AF state.

As shown in FIG. 6B, the transition probability matrix 502 includes the two states, NSR and AF, and probabilities that the subject 306 will remain in a current state or transition to a different state. For example, when the subject 306 is in the NSR state, there is a 90% probability that the subject 306 will remain in the NSR state from one time step to a next time step. In the AF burden estimation operation 310, the time steps can be any suitable duration, although a few hours to a couple of days is typical.

As shown in FIG. 6C, the emission probability matrix 503 includes the two states, NSR and AF, and probabilities that depend on different observations. In FIG. 6C, the observations are a combination of a decision regarding the subject 306 and an activity level of the subject 306. Looking at the first row of the emission probability matrix 503, if the mobile device 302 obtains or generates an AF decision about the subject 306, and the subject 306 is at rest, there is a 30% probability that the subject 306 is actually in an NSR (i.e., normal) condition and a 70% probability that the subject 306 is in an AF condition. Looking at the third row of the emission probability matrix 503 (observation=AF Decision, Running), when the subject 306 is running, the probability that the subject 306 is in an AF condition reduces to 40%, because the subject's heart rate is elevated from running and the readings from the sensors 304 may be noisier due to greater movement. This reduces the confidence of the AF decision being correct.

Predetermined demographic information of the subject 306 (e.g., gender, age, race, ethnic group, weight, lifestyle, prior medical history, and the like) can be used to determine initial values for the probabilities in the prior probability matrix 501 and the transition probability matrix 502. For example, in FIG. 6A, the initial values for the prior probability matrix 501 can be determined or defined even if there is no prior information for the subject 306 from the sensors 304. In some embodiments, the initial values $\pi_{AF}=0.2$ and $\pi_{NSR}=0.8$ can be predetermined based on general population characteristics, such as according to the following equations:

$$\pi_{AF}=(0.05\times\gamma)+0.0015 \tag{1}$$

$$\pi_{NSR}=1-\pi_{AF} \tag{2}$$

where $\gamma$ is the total $CHA_2DS_2$-VASc score for the subject 306. The $CHA_2DS_2$-VASc score is a single scalar score that takes into account congestive heart failure (C), hypertension (H), age greater than 75 years ($A_2$), diabetes mellitus (D), prior stroke or thromboembolism ($S_2$), vascular disease (V), age between 65-74 (A), and sex category (or gender) (Sc). The more of these factors that a person has, the more likely of a serious outcome from AF, and the higher the score. If one or more of these factors are not specifically known for the subject 306, then the initial values for the prior probability matrix 501 can be initialized based on general population estimates.

In FIG. 6B, a formula based on the previous day's AF burden and the time between successive HMM states can be used to develop initial values for the transition probability matrix 502. Stated differently, the trend from the previous day will guide the current day. This leverages the fact that these rhythms are typically slow-changing in the subject 306. That is, the transition from AF to normal or normal to AF is not likely to be sudden; it will usually happen over a period of time. A shorter time between successive states means increased likelihood of remaining in the same rhythm. In some embodiments, the initial probability values for the transition probability matrix 502 can be determined according to the following equations:

$$S_{AF-AF} = \min\left(\mu \times \frac{\theta}{t}, 0.95\right) \tag{3}$$

$$S_{NSR-NSR} = \min\left((1-\mu) \times \frac{\theta}{t}, 0.95\right) \tag{4}$$

$$S_{AF-NSR} = 1 - S_{AF-AF} \tag{5}$$

$$S_{NSR-AF} = 1 - S_{NSR-NSR} \tag{6}$$

where $\mu$ is the AF burden from the previous day (normalized to be between 0 and 1), t is the time between successive time steps in the HMM architecture 400, and $\theta$ is a normalizing constant.

In FIG. 6C, the initial values for the probabilities in the emission probability matrix 503 can be heuristically initialized depending on the number and nature of available observation sources and preexisting knowledge of AF decision algorithm characteristics. Thus, the initialization can change depending on the sensors 304 that are used. In FIG. 6C, the emission probability matrix 503 only reflects two observation sources: an AF detection algorithm executed on a smart device (e.g., a smart watch) and an activity detection module that detects if the subject 306 is running. In actual implementations, the emission probability matrix 503 is likely to include additional observation sources and additional possible observations.

The observations can be generated from a wide variety of observation sources, such as the on-device AF detection algorithm, IMU sensor observations (e.g., activity, running, walking, reclining, etc.), subject risk factors (e.g., age, hypertension, diabetes, etc.), detection of irregular heart rhythms (e.g., premature ventricular contractions (PVCs), premature atrial contractions (PACs), etc.), and the like.

Knowledge of the observation sources can be used to determine the weights of their contributions to each state. For example, if the AF detection algorithm has very high specificity, there can be more weight placed on the NSR state when there is an NSR decision. In some embodiments, weights can be assigned to the type of sensor 304. For example, heart rhythm sensors are typically very important in AF burden determination, so such sensors can be assigned a high weight. Activity sensors capable of detecting that the subject 306 is running may be somewhat important, and can be assigned a medium weight. Location sensors, such that those that detect that the subject 306 is inside or outside, may not be very important and can be assigned a low weight.

In some embodiments, the mobile device 302 performs the AF burden estimation operation 310 regularly or continuously for a long period of time (albeit with some possible temporal gaps, as discussed above). For example, the mobile device 302 can perform the AF burden estimation operation 310 over days, weeks, or months, which can comprise dozens or hundreds of time steps in the HMM architecture 400. As the AF burden estimation operation 310 is performed over time, at each time step, new sensor observations 308 can be collected based on new data from the sensors 304. At certain intervals (e.g., at each time step), the mobile device 302 can update the probabilities in the transition probability matrix 502 and the emission probability matrix 503 based on the updated sensor observations 308. Thus, it is not necessary to calibrate the mobile device 302 to the subject 306 to start the AF burden estimation operation 310, and the AF burden estimation operation 310 automatically becomes personalized to the subject 306 over time.

The HMM architecture 400 can be established and updated for the AF burden estimation operation 310 taking into account the following factors that are unique to AF burden:

1. Changes in state for the subject 306 are unlikely to be sudden and volatile over short periods of time, such as a 15-minute window. The probability values of the transition probability matrix 502 can be tuned in view of this.

2. Formulation of the HMM architecture 400 is important not only to estimate the overall burden for a given day, but also to easily determine the longest contiguous AF episode, which is clinically significant information.

Given longitudinal measurement (over a period of days or weeks), the mobile device 302 will learn the underlying HMM architecture 400 and fill in data gaps for times when AF information is unavailable or inaccurate. A larger combination of multiple sources of observation can increase the accuracy of filling data gaps in the HMM architecture 400.

Once the matrices 501-503 are initialized, the mobile device 302 can execute one or more algorithms to determine the most probable sequence of AF states for the subject 306. For example, in some embodiments, the mobile device 302 can execute a Viterbi algorithm to determine a probable sequence of AF states for the subject 306 over a time period (e.g., over one day).

As known in the art, a Viterbi algorithm can be used to find a most probable sequence of states Q, given an input HMM with a transition probability matrix A, an emission probability matrix B, and a sequence of observations O. Initialization of the Viterbi algorithm can be performed by determining the probability of each possible state in the first time step, as in the following equation:

$$v_1(j) = \pi_j b_j(o_1), j \in \{\alpha, \beta, \ldots, N\}. \quad (7)$$

After initialization, the Viterbi algorithm can include one or more recursive steps, in which the probability of each possible state at time step 't' can be determined, such as in the following equation:

$$v_t(j) = \max_{i=1 \text{ to } N} v_{t-1}(i) s_{ij} b_j(o_t). \quad (8)$$

In the context of the AF burden estimation operation 310, the mobile device 302 can execute a Viterbi algorithm to enable the estimation of the AF state of the subject 306 when there are gaps or noisy signal information in the sensor observations 308. For the AF burden estimation operation 310, the mobile device 302 leverages the probability matrices 501-503 when executing the Viterbi algorithm.

In some embodiments, the mobile device 302 can execute a Baum-Welch algorithm, which is, in some ways, the reverse of the Viterbi algorithm. As known in the art, a Baum-Welch algorithm provides a technique to update the HMM matrices based on actual observations. Given an observation sequence O, and a set of states in the HMM, the Baum-Welch algorithm can be used to learn the transition probability matrix A and the emission probability matrix B.

In the context of the AF burden estimation operation 310, the mobile device 302 can execute a Baum-Welch algorithm to enable the dynamic update of the probability matrices 501-503 based on the heart rhythm or other health parameters of the subject 306 over the course of each day. Upon definition of a time scale for the Baum-Welch algorithm, the mobile device 302 can cyclically execute the Baum-Welch algorithm in the time scale, as well as the update cap.

Figure 7A:
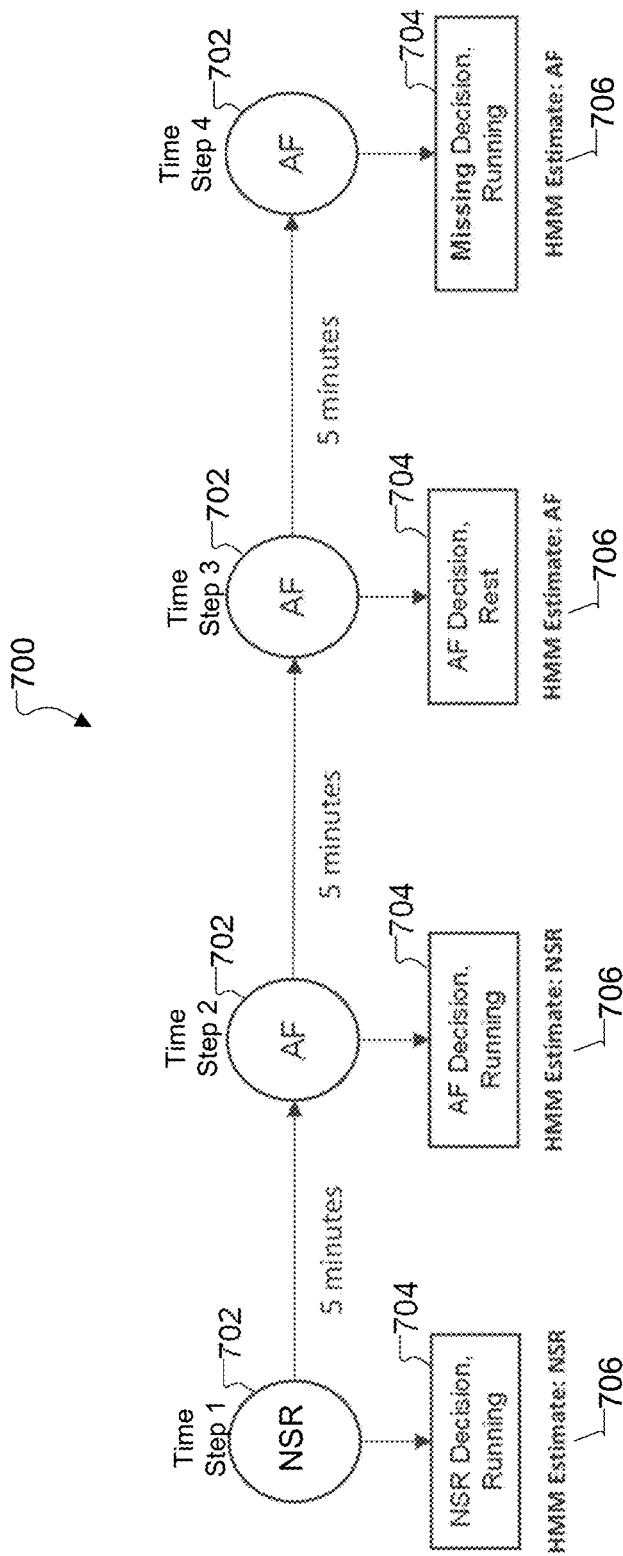
FIGS. 7A and 7B illustrate an example of updating probability matrices for use in AF burden estimation, in accordance with this disclosure.
Figure 7B:
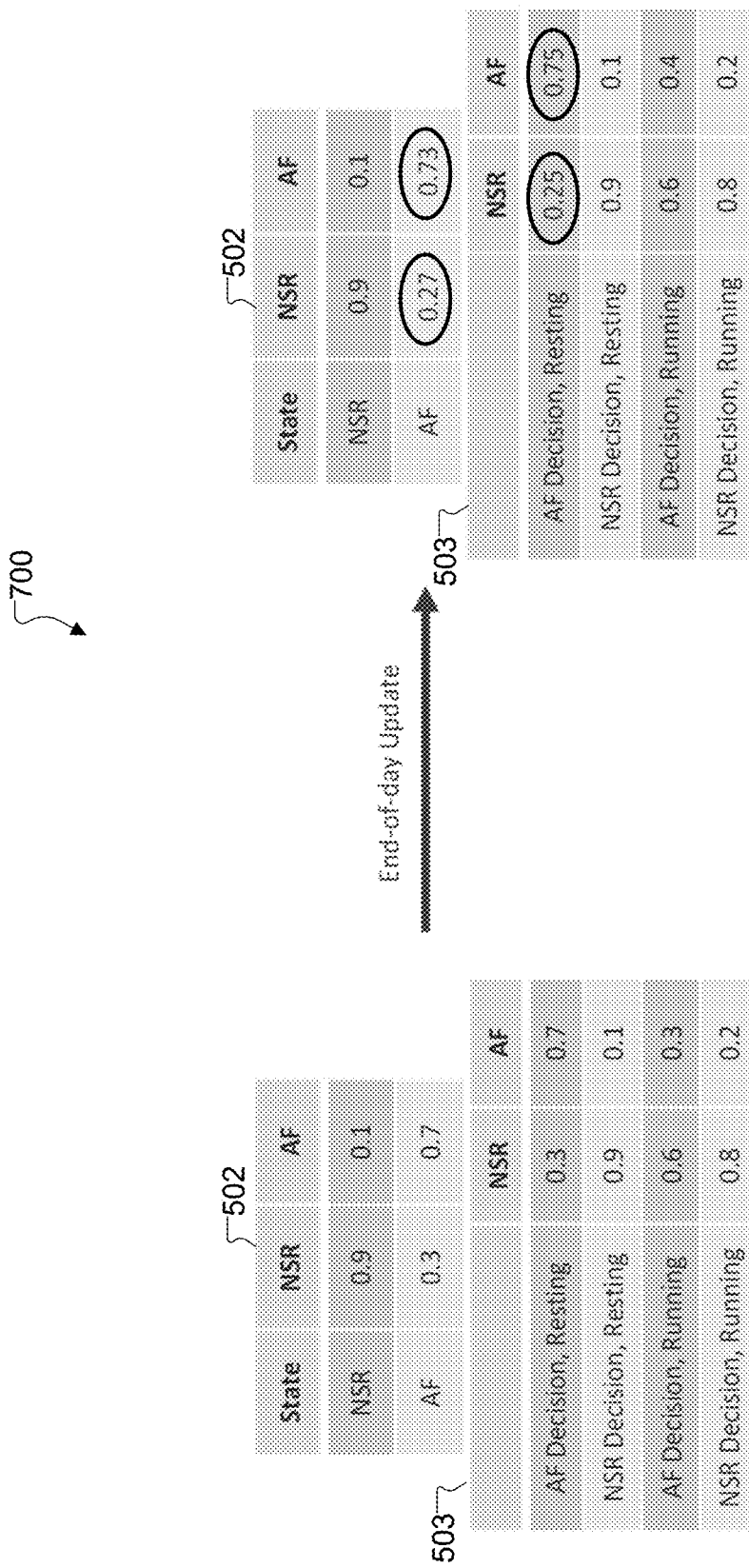

FIGS. 7A and 7B illustrate an example 700 of updating probability matrices for use in the AF burden estimation operation 310, in accordance with this disclosure. As shown in FIG. 7A, multiple AF states 702 of the subject 306 are shown at different time steps, where consecutive time steps are separated by approximately five minutes. The AF states 702 represent the true AF state of the subject 306 at each time step. For example, at time step 1, the AF state 702 indicates that the subject 306 is actually in a NSR state. This true state may not be readily available to the mobile device 302.

Also associated with each time step is one or more observations 704 that can be used by the mobile device 302 in the AF burden estimation operation 310. Each observation 704 can represent, or be represented by, one of the observations in the emission probability matrix 503. For example, at time step 1, the observations 704 of the subject 306 are an NSR decision regarding the subject 306 and a running activity level of the subject 306. In addition to the observations 704, each time step is associated with an estimated state 706 that is determined by the mobile device 302 while performing the AF burden estimation operation 310. For example, at time step 1, the mobile device 302 estimates an NSR state 706 for the subject 306.

At time step 2, the true AF state 702 of the subject 306 has changed from NSR to AF, and the observations 704 of the subject 306 include an AF decision and a running activity. Although the true AF state 702 is now AF, the mobile device 302 continues to determine an estimated state 706 of NSR at time step 2. In the example 700, the emission probability based on the 'running' observation 704 causes the mobile device 302 to delay an estimated state 706 of AF. This could be due to the fact that running elevates the heart rate and thus reduces the overall likelihood of a true AF state simply based on an 'AF decision' observation 704.

At time step 3, the true AF state 702 of the subject 306 remains at AF, and the observations 704 of the subject 306 include an AF decision and a rest activity. Since the subject 306 is now at rest, and an elevated heart rate due to running is no longer a factor, the mobile device 302 is more like to trust the 'AF decision' observation 704; thus, the mobile device 302 determines an estimated state 706 of AF.

At time step 4, the true AF state 702 of the subject 306 remains at AF, and the observations 704 of the subject 306 include a running activity. However, there is a missing observation 704 related to 'AF decision' or 'NSR decision'. This missing observation 704 could be due to a gap in sensor information or the sensor information could be noisy. Use of the Viterbi algorithm allows the mobile device 302 to determine an estimated state 706 at time step 4, even though data is missing or noisy. In some embodiments, the mobile device 302 can tolerate gaps of up to 2 hours continuously, or 8 hours per day overall without significant error in determination of estimated states 706.

At the end of a predetermined time period (e.g., at the end of each day), the mobile device 302 can use the Baum-Welch algorithm to update one or more probability values in the transition probability matrix 502, the emission probability matrix 503, or both, based on the data from the subject 306. For example, as shown in FIG. 7B, the circled values in the transition probability matrix 502 and the emission probability matrix 503 have been updated at the end of the day. In some embodiments, the mobile device 302 does not update any probability values by more than 10% (or another suitable threshold cap) to ensure that the probabilities do not over-fit to one day's data.

Turning again to FIG. 3, once the mobile device 302 has estimated the AF burden of the subject 306 using the AF burden estimation operation 310, the mobile device 302 can perform an AF burden notification operation 312. The mobile device 302 can perform the AF burden notification operation 312 to notify the subject 306 of changes in the subject's AF burden while taking into consideration context information to ensure that the information is as reliable as possible and that the presentation of the information will not unduly affect the subject's physiological state.

Figure 8:
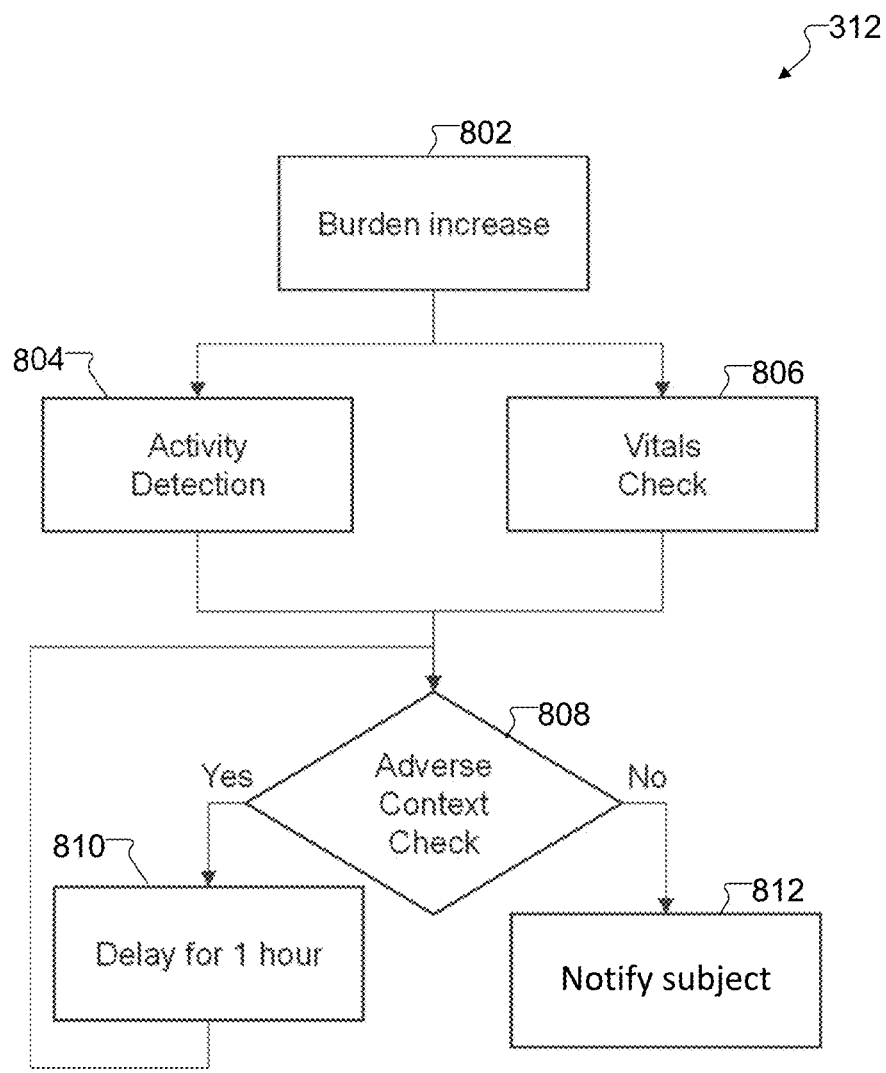
FIG. 8 illustrates an example of AF burden notification in accordance with this disclosure.

FIG. 8 illustrates an example of the AF burden notification operation 312 in accordance with this disclosure. As shown in FIG. 8, the subject 306 may exhibit a significant increase 802 in their average AF burden over time, which the mobile device 302 can detect by performing the AF burden estimation operation 310. For example, in some embodiments, the increase 802 may be a 10% increase in AF burden compared to a previous time period (e.g., the time of the last notification).

Due to the significant increase 802, the subject 306 may need to be informed of this adverse event through a notification. However, receiving new adverse information regarding AF may inadvertently affect stress and blood pressure in the subject 306, as AF is closely associated with these physiological parameters. In addition, the subject's current activity level can also indicate whether the AF burden increase 802 is truly significant or an anomaly due to high activity level. Accordingly, the mobile device 302 can generate the notification while taking into account estimates of stress, blood pressure, and current activity level of the subject 306.

In some embodiments, before the mobile device 302 notifies the subject 306 of the AF burden increase 802, the mobile device 302 determines (at activity detection operation 804) the current activity level of the subject 306. For example, the mobile device 302 can receive sensor information to determine if the subject 306 is running. The mobile device 302 also performs a vitals check 806 of the subject 306. For example, the mobile device 302 can receive stress and heart rate variability (HRV) information of the subject 306, and blood pressure information of the subject 306 that is measured, e.g., using a PPG sensor.

The mobile device 302 then performs an adverse context check 808 based on the received information. If the mobile device 302 determines that the subject 306 is currently running, or if the stress level of the subject 306 is high, or if the subject 306 is currently hypertensive, then the mobile device 302 does not notify the subject 306 immediately, but instead waits for a delay period 810 (e.g., one hour). This is acceptable because a 10% increase in AF burden does not typically require immediate medical intervention, and hence it is preferable to delay the information delivery to a suitable later time when the subject 306 is best conditioned to receive the information. The mobile device 302 checks every hour if all conditions of the subject 306 are met (e.g., at rest, normal stress, normal BP, etc.) before providing a notification 812 to the subject 306. It is noted that AF patients typically have a baseline HRV that is lower than the general population, so the threshold for HRV-based stress detection can be adjusted accordingly in some embodiments.

Referring back to FIG. 3, in addition to the mobile device 302 performing the AF burden notification operation 312, the mobile device 302 can perform an AF burden recommendation operation 314.

In the AF burden recommendation operation 314, the mobile device 302 can determine and output one or more AF burden recommendations that are personalized for the subject 306. In general, AF burden is associated with personal health factors, such as weight, blood pressure, sedentary lifestyle, stress level, and the like. Some of these health factors can be influenced by lifestyle choices. Thus, the mobile device 302 can provide recommendations of lifestyle choices to the subject 306 to reduce AF burden. Given the knowledge of previous history and contexts of burden changes as obtained in the AF burden estimation operation 310, the mobile device 302 can provide recommendations that are personalized to the individual subject 306. For example, the mobile device 302 can provide a recommendation to, e.g., go for a jog to increase activity level, do yoga to reduce stress, or the like.

Figure 9:
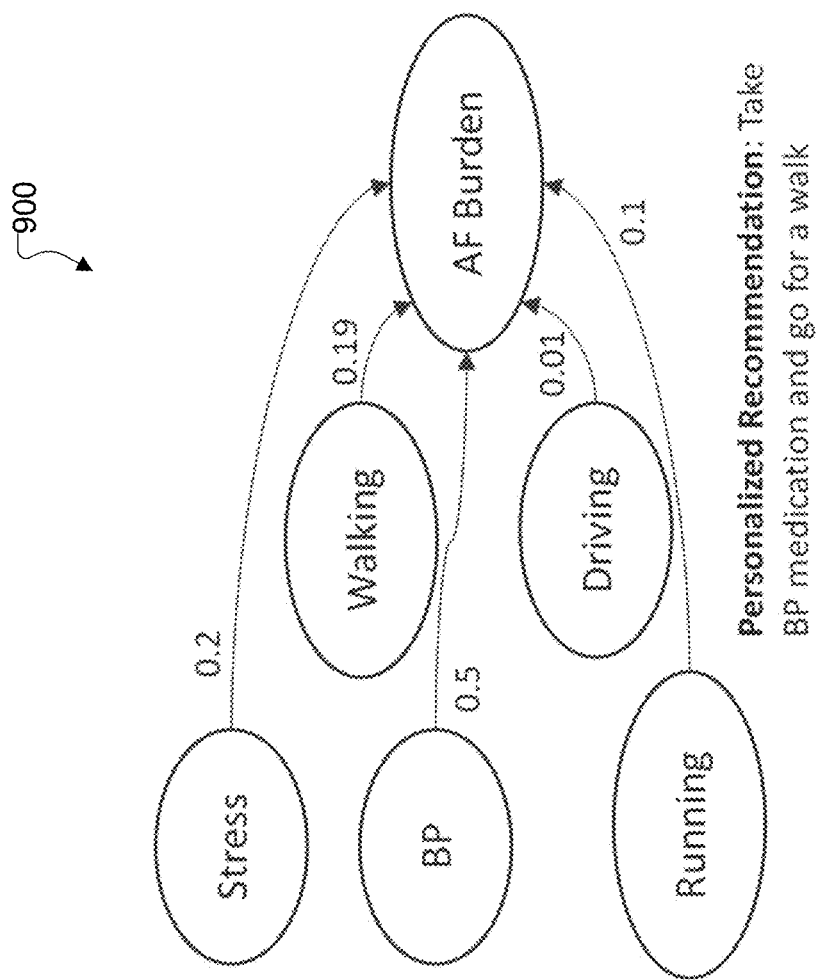
FIG. 9 illustrates an example diagram showing various health factors and activities that affect a level of AF burden in a subject, in accordance with this disclosure.

For example, FIG. 9 illustrates an example diagram 900 showing various health factors and activities that affect a level of AF burden in the subject 306, in accordance with this disclosure. As shown in FIG. 9, one or more sensors 304 can measure stress, blood pressure, and activity of the subject 306, such as walking, running, or driving. The influence of these health factors and activities on the AF burden can vary among individual subjects, thus different weights can be assigned to the factors in a manner that is unique for the subject 306. For example, in FIG. 9, blood pressure of the subject 306 can have a significant impact on AF burden, so blood pressure is assigned a weight of 0.5. Stress may have less of an impact on AF burden for the subject 306, so stress is assigned a lower weight of 0.2.

In some embodiments, the mobile device 302 can use a Causal Bayesian Network to determine the weights for each of the links between these health factors/activities and the AF burden. As known in the art, Causal Bayesian Networks present a very explainable relationship between an event and various causes, which is important in the context of health applications. In the context of the process 300, a Causal Bayesian Network allows derivation of the posterior probability distribution given the event (e.g., AF burden increase). Given sufficient data (which can be expected in the daily continuous monitoring scenario of the process 300), the Causal Bayesian Network can be constructed and updated automatically.

Figure 10:
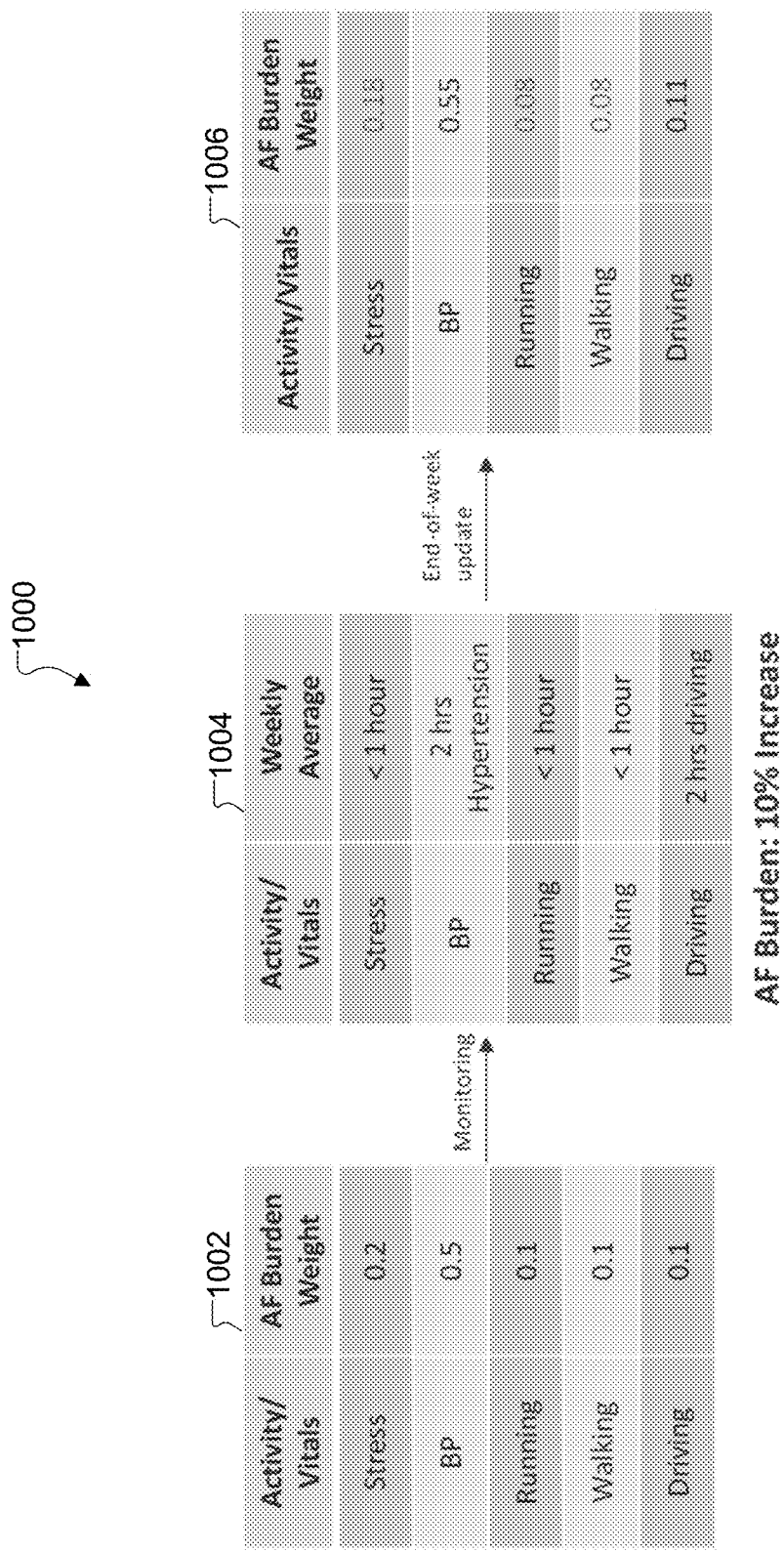
FIG. 10 illustrates an example of monitoring health factors and activities over time to determine one or more AF burden recommendations, in accordance with this disclosure.

FIG. 10 illustrates an example 1000 of monitoring health factors and activities over time to determine one or more AF burden recommendations, in accordance with this disclosure. As shown in FIG. 10, a table 1002 includes a predetermined set of health factors and activities that are associated with the subject 306 and are monitored by the mobile device 302. The health factors and activities listed in the table 1002 are the same as the health factors and activities shown in the diagram 900 of FIG. 9. The influence or weight of these health factors and activities on AF burden are initialized in the table 1002 based on prior knowledge.

The table 1004 shows the health factors and activities, and how much the subject 306 was engaged in the activity or subject to the health factor, on average each day over a week period. The values in the table 1004 are based on information obtained by the mobile device 302 during passive monitoring over the week while the subject 306 was in a free-living environment. For each day, a given activity is considered to have significant influence if the subject 306 was engaged in the activity for more than 1 hour. Similarly, a given health factor is significant if the subject 306 was in an abnormal state for more than 1 hour. Based on the information in the table 1004, it is determined that the subject 306 had about 2 hours of hypertension per day, and participated in driving about 2 hours per day, but did not spend much time running or walking each day. Also, stress was not a significant factor each day for the subject 306.

At the end of the week, if there is at least a 10% change in AF burden of the subject 306 compared to the previous week, the weights of one or more activities or health factors in the table 1002 can be adjusted accordingly. For example, the table 1006 is an updated version of the table 1002 after the weights have been adjusted. In the example 1000, high incidences of hypertension and driving during the day appear to correlate with the 10% increase in AF burden. Thus, the mobile device 302 increases the weights of blood pressure and driving by 10% and lowers the weights of the other factors by a proportional amount. The weights can also affect the personalized recommendation that the mobile device 302 outputs to the subject 306. For example, the mobile device 302 may instruct the subject 306 to control blood pressure with medication and reduce driving each day. As discussed above, in some embodiments, the mobile device 302 does not update any weight values by more than 10% (or another suitable threshold cap) to ensure that the probabilities do not over-fit to one day's data.

In the example 1000 shown in FIG. 10, the time scales are selected with the knowledge that there is low temporal relationship between the listed health factors or activities and lasting changes in AF burden. Of course, other embodiments could include other time scale values.

In some embodiments, AF burden information of the subject 306 can be additionally or alternatively estimated by one or more other devices, such as medical grade devices (e.g., a Holter monitor, an invasive rhythm detector, and the like), another consumer electronic device, or any other suitable sensor-enabled device. In such embodiments, the mobile device 302 can receive the estimated AF burden information obtained from the other device(s), and use the information to determine and provide personalized, context-informed notifications or recommendations to the subject 306.

In some embodiments, the mobile device 302 can notify a medical provider (e.g., a physician) with one or more AF burden estimates of the subject 306 in order for the provider to make lifestyle recommendations to the subject 306. For example, the provider may recommend more walking for the subject 306. The mobile device 302 can then monitor the effectiveness of the recommended recommendation in terms of its effect on AF burden reduction in the subject 306. In some embodiments, the mobile device 302 can detect the occurrence of activities prescribed by the medical provider, and compare it to the AF burden changes on successive days. If these two factors are uncorrelated (e.g., r<0.2), the regimen can be said to be ineffective. For example, the mobile device 302 may detect that the subject 306 walked more (as recommended), but the AF burden was unchanged or changed very little. The mobile device 302 can generate an effectiveness report, which can be provided to the medical provider for changing or fine-tuning the proposed regimen.

Although FIGS. 3 through 10 illustrate example details of a process 300 for AF burden estimation, notification, and management, various changes may be made to FIGS. 3 through 10. For example, rather than the process 300 using a HMM, other techniques can be used, such as a Kalman filter or particle filter. In addition, various operations in FIGS. 3 through 10 could overlap, occur in parallel, occur in a different order, or occur any number of times. Also, the specific operations shown in FIGS. 3 through 10 are examples only, and other techniques could be used to perform each of the operations shown in FIGS. 3 through 10.

It should be noted that the various functions and operations shown and described above with respect to FIGS. 3 through 10 can be implemented in the mobile device 302 (which could include any of the electronic devices 101, 102, 104 or the server 106) in any suitable manner. For example, in some embodiments, at least some of the functions and operations can be implemented or supported using one or more software applications or other software instructions that are executed by the processor(s) 120, 240 of the electronic device(s). In other embodiments, at least some of the functions and operations can be implemented or supported using dedicated hardware components. In general, the functions and operations can be performed using any suitable hardware or any suitable combination of hardware and software/firmware instructions. Also, computing and communication systems come in a wide variety of configurations, and FIGS. 3 through 10 do not limit the scope of this disclosure to any particular configuration.

Figure 11:
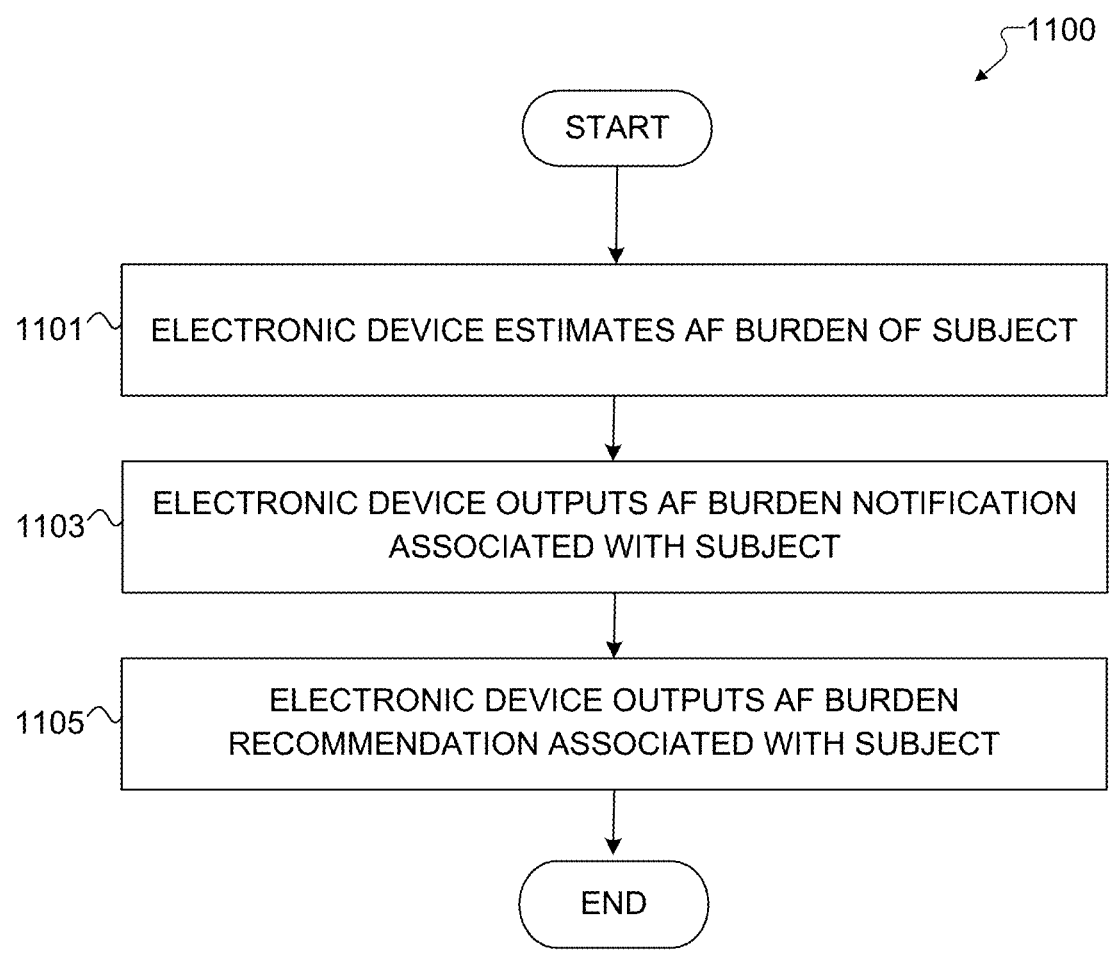
FIG. 11 illustrates an example method for AF burden estimation, notification, and management in accordance with this disclosure.

FIG. 11 illustrates an example method 1100 for AF burden estimation, notification, and management in accordance with this disclosure. For ease of explanation, the method 1100 shown in FIG. 11 is described as involving the process 300 shown in FIG. 3. The method 1100 may be performed by an electronic device, such as the electronic device 101 of FIG. 1. However, the method 1100 could involve any other suitable process and be performed by any suitable device or system without departing from the scope of this disclosure.

At operation 1101, a consumer electronic device estimates an AF burden of a subject based on multiple measurements passively collected by at least one sensor associated with the consumer electronic device over a time period while the subject is in a free-living environment. This can include, for example, the mobile device 302 estimating the AF burden of the subject 306 by performing the AF burden estimation operation 310 of FIG. 3.

In some embodiments, the consumer electronic device estimates the AF burden by obtaining a first sequence of state values based on the multiple measurements collected by the at least one sensor, the first sequence of state values including detected AF states and detected normal sinus rhythm (NSR) states of the subject; obtaining a transition probability matrix, the transition probability matrix indicating a probability of state transition between an AF state and a NSR state; obtaining an emission probability matrix, the emission probability matrix indicating a probability of one or more observations arising from an estimated AF state or an estimated NSR state; and estimating a second sequence of state values based on the first sequence of state values, the transition probability matrix, and the emission probability matrix, wherein the second sequence of state values include at least one estimated state value that is different from the detected AF states or the detected NSR states.

In some embodiments, the consumer electronic device further estimates the AF burden by initializing a prior probability matrix, the prior probability matrix indicating a probability of a starting state of the subject being the AF state or the NSR state, wherein the transition probability matrix is based on the prior probability matrix; and updating the transition probability matrix based on a determined AF burden from a previous time period and an amount time elapsed between consecutive values of the second sequence of state values.

In some embodiments, the consumer electronic device further estimates the AF burden by assigning weights to at least some of the multiple measurements collected by the at least one sensor and activities of the subject; and upon detection of a change in the estimated AF burden exceeding a threshold value within a time duration, updating the weights based on a duration of the activities or a duration of the at least some measurements being abnormal.

At operation 1103, the consumer electronic device outputs an AF burden notification associated with the subject based on the estimated AF burden. This can include, for example, the mobile device 302 outputting an AF burden notification by performing the AF burden notification operation 312 of FIG. 3.

In some embodiments, the consumer electronic device outputs an AF burden notification associated with the subject by notifying the subject upon detection of an increase in an average of the estimated AF burden that is greater than a threshold value. In some embodiments, the consumer electronic device outputs an AF burden notification associated with the subject by notifying a medical provider of the estimated AF burden of the subject, the estimated AF burden enabling the medical provider to make a health recommendation to the subject.

At operation 1105, the consumer electronic device outputs an AF burden recommendation based on the estimated AF burden. This can include, for example, the mobile device 302 outputting an AF burden recommendation by performing the AF burden recommendation operation 314.

In some embodiments, the consumer electronic device outputs the AF burden recommendation by outputting, on a display communicatively coupled to the consumer electronic device, a recommendation to the subject to change at least one activity by the subject.

Although FIG. 11 illustrates one example of a method 1100 for AF burden estimation, notification, and management in accordance with this disclosure, various changes can be made to FIG. 11. For example, various steps in FIG. 11 could overlap, occur in parallel, occur serially, occur in a different order, or occur any number of times. Also, the steps of the method 1100 could be implemented in any suitable manner, such as entirely within the electronic device 101 or using a combination of devices. For instance, as indicated above, electronic device 101 could collect data and provide the data to a server 106, which could then process the data and generate any suitable output.

Although this disclosure has been described with reference to various example embodiments, various changes and modifications may be suggested to one skilled in the art. It is intended that this disclosure encompass such changes and modifications as fall within the scope of the appended claims.

What is claimed is:

1. A method, comprising:
estimating, by a consumer electronic device, an atrial fibrillation (AF) burden of a subject based on multiple measurements passively collected by at least one sensor associated with the consumer electronic device while the subject is in a free-living environment;
outputting, by the consumer electronic device, an AF burden notification associated with the subject based on the estimated AF burden; and
outputting, by the consumer electronic device, an AF burden recommendation based on the estimated AF burden;
wherein estimating the AF burden comprises:
obtaining a first sequence of state values based on the multiple measurements collected by the at least one sensor, the first sequence of state values including past detected AF states and past detected normal sinus rhythm (NSR) states of the subject;
obtaining a transition probability matrix comprising values indicating probabilities of state transitions between an AF state and a NSR state;
obtaining an emission probability matrix comprising values indicating probabilities of one or more estimated AF states or one or more estimated NSR states arising from multiple observations; and
estimating a second sequence of state values based on the first sequence of state values, the transition probability matrix, and the emission probability matrix.

2. The method of claim 1, wherein estimating the AF burden further comprises:
initializing a prior probability matrix, the prior probability matrix indicating a probability of a starting state of the subject being the AF state or the NSR state, wherein the transition probability matrix is based on the prior probability matrix; and updating the transition probability matrix based on a determined AF burden from a previous time period and an amount time elapsed between consecutive values of the second sequence of state values.

3. The method of claim 1, wherein estimating the AF burden further comprises:

assigning weights to at least some of the multiple measurements collected by the at least one sensor and activities of the subject; and upon detection of a change in the estimated AF burden exceeding a threshold value within a time duration, updating the weights based on a duration of the activities or a duration of the at least some measurements being abnormal.

4. The method of claim 1, wherein outputting the AF burden notification associated with the subject comprises:

obtaining at least one measurement of a vitals check of the subject; and when the at least one measurement is within a threshold range, notifying the subject upon detection of an increase in an average of the estimated AF burden that is greater than a threshold value.

5. The method of claim 1, wherein outputting the AF burden notification associated with the subject comprises:

notifying a medical provider of the estimated AF burden of the subject, the estimated AF burden enabling the medical provider to make a health recommendation to the subject.

6. The method of claim 1, wherein outputting the AF burden recommendation comprises:

outputting, on a display communicatively coupled to the consumer electronic device, a recommendation to the subject to change at least one activity by the subject.

7. The method of claim 1, wherein the at least one sensor comprises at least two of an inertial measurement unit (IMU) sensor, a photoplethysmogram (PPG) sensor, and a global positioning system (GPS) sensor.

8. An electronic device comprising:

at least one memory configured to store instructions; and at least one processor configured when executing the instructions to:

estimate an atrial fibrillation (AF) burden of a subject based on multiple measurements passively collected by at least one sensor associated with the electronic device while the subject is in a free-living environment;

output an AF burden notification associated with the subject based on the estimated AF burden; and output an AF burden recommendation based on the estimated AF burden;

wherein the electronic device is a consumer electronic device; and wherein, to estimate the AF burden, the at least one processor is configured to:

obtain a first sequence of state values based on the multiple measurements collected by the at least one sensor, the first sequence of state values including past detected AF states and past detected normal sinus rhythm (NSR) states of the subject;

obtain a transition probability matrix comprising values indicating probabilities of state transitions between an AF state and a NSR state;

obtain an emission probability matrix comprising values indicating probabilities of one or more estimated AF states or one or more estimated NSR states arising from multiple observations; and estimate a second sequence of state values based on the first sequence of state values, the transition probability matrix, and the emission probability matrix.

9. The electronic device of claim 8, wherein, to estimate the AF burden, the at least one processor is further configured to:

initialize a prior probability matrix, the prior probability matrix indicating a probability of a starting state of the subject being the AF state or the NSR state, wherein the transition probability matrix is based on the prior probability matrix; and update the transition probability matrix based on a determined AF burden from a previous time period and an amount time elapsed between consecutive values of the second sequence of state values.

10. The electronic device of claim 8, wherein the at least one processor is further configured to:

assign weights to at least some of the multiple measurements collected by the at least one sensor and activities of the subject; and upon detection of a change in the estimated AF burden exceeding a threshold value within a time duration, update the weights based on a duration of the activities or a duration of the at least some measurements being abnormal.

11. The electronic device of claim 8, wherein, to output the AF burden notification associated with the subject, the at least one processor is configured to:

obtain at least one measurement of a vitals check of the subject; and when the at least one measurement is within a threshold range, notify the subject upon detection of an increase in an average of the estimated AF burden that is greater than a threshold value.

12. The electronic device of claim 8, wherein, to output the AF burden notification associated with the subject, the at least one processor is configured to:

notify a medical provider of the estimated AF burden of the subject, the estimated AF burden enabling the medical provider to make a health recommendation to the subject.

13. The electronic device of claim 8, wherein, to output the AF burden recommendation, the at least one processor is configured to:

control a display communicatively coupled to the consumer electronic device to output a recommendation to the subject to change at least one activity by the subject.

14. The electronic device of claim 8, wherein the at least one sensor comprises at least two of an inertial measurement unit (IMU) sensor, a photoplethysmogram (PPG) sensor, and a global positioning system (GPS) sensor.

15. A non-transitory computer readable medium containing computer readable program code that, when executed, causes at least one processor of an electronic device to:

estimate an atrial fibrillation (AF) burden of a subject based on multiple measurements passively collected by at least one sensor associated with the electronic device while the subject is in a free-living environment;

output an AF burden notification associated with the subject based on the estimated AF burden; and output an AF burden recommendation based on the estimated AF burden;

wherein the electronic device is a consumer electronic device; and wherein the computer readable program code that when executed causes the at least one processor to estimate the AF burden comprises:
computer readable program code that when executed causes the at least one processor to:
obtain a first sequence of state values based on the multiple measurements collected by the at least one sensor, the first sequence of state values including past detected AF states and past detected normal sinus rhythm (NSR) states of the subject;
obtain a transition probability matrix comprising values indicating probabilities of state transitions between an AF state and a NSR state;
obtain an emission probability matrix comprising values indicating probabilities of one or more estimated AF states or one or more estimated NSR states arising from multiple observations; and
estimate a second sequence of state values based on the first sequence of state values, the transition probability matrix, and the emission probability matrix.

16. The non-transitory computer readable medium of claim 15, wherein the computer readable program code that when executed causes the at least one processor to estimate the AF burden further comprises computer readable program code that when executed causes the at least one processor to:
initialize a prior probability matrix, the prior probability matrix indicating a probability of a starting state of the subject being the AF state or the NSR state, wherein the transition probability matrix is based on the prior probability matrix; and
update the transition probability matrix based on a determined AF burden from a previous time period and an amount time elapsed between consecutive values of the second sequence of state values.

17. The non-transitory computer readable medium of claim 15, wherein the computer readable program code when executed further causes the at least one processor to:
assign weights to at least some of the multiple measurements collected by the at least one sensor and activities of the subject; and
upon detection of a change in the estimated AF burden exceeding a threshold value within a time duration, update the weights based on a duration of the activities or a duration of the at least some measurements being abnormal.

18. The non-transitory computer readable medium of claim 15, wherein the computer readable program code that when executed causes the at least one processor to output the AF burden notification associated with the subject comprises computer readable program code that when executed causes the at least one processor to:
obtain at least one measurement of a vitals check of the subject; and
when the at least one measurement is within a threshold range, cause the electronic device to notify the subject upon detection of an increase in an average of the estimated AF burden that is greater than a threshold value.

19. The non-transitory computer readable medium of claim 15, wherein the computer readable program code that when executed causes the at least one processor to output the AF burden recommendation comprises:
computer readable program code that when executed causes the at least one processor to control a display communicatively coupled to the electronic device to output a recommendation to the subject to change at least one activity by the subject.

20. The non-transitory computer readable medium of claim 15, wherein the at least one sensor comprises at least two of an inertial measurement unit (IMU) sensor, a photoplethysmogram (PPG) sensor, and a global positioning system (GPS) sensor.

* * * * *